United States Patent [19]

Razavi

[11] Patent Number: 5,292,838

[45] Date of Patent: *Mar. 8, 1994

[54] PROCESS AND CATALYST FOR PRODUCING SYNDIOTACTIC POLYMERS

[75] Inventor: Abbas Razavi, Patourage, Belgium

[73] Assignee: Fina Technology, Inc., Dallas, Tex.

[*] Notice: The portion of the term of this patent subsequent to Mar. 31, 2009 has been disclaimed.

[21] Appl. No.: 66,890

[22] Filed: May 25, 1993

Related U.S. Application Data

[60] Division of Ser. No. 876,714, Apr. 24, 1991, Pat. No. 5,223,467, which is a continuation of Ser. No. 418,497, Oct. 10, 1989, abandoned, which is a continuation-in-part of Ser. No. 220,007, Jul. 15, 1988, Pat. No. 4,892,851.

[51] Int. Cl.$^5$ .............................................. C08F 4/642
[52] U.S. Cl. .................................. 526/160; 502/152; 526/170
[58] Field of Search .......................................... 526/160

[56] References Cited

U.S. PATENT DOCUMENTS

| | | | |
|---|---|---|---|
| 3,135,809 | 6/1964 | Bosmajian | 502/103 |
| 3,305,538 | 2/1967 | Natta et al. | 260/93.7 |
| 3,364,190 | 1/1968 | Emrick | 260/93.7 |
| 4,658,078 | 4/1987 | Staugh et al. | 585/523 |

FOREIGN PATENT DOCUMENTS

| | | |
|---|---|---|
| 227003 | 8/1988 | European Pat. Off. . |
| 227004 | 8/1988 | European Pat. Off. . |

OTHER PUBLICATIONS

Zambelli, A. et al., "Isotactic Polymerization of Propene: Homogenous Catalysts Based on Group 4 Metallocenes Without Methylaluminoxane:", Macro-Molecule 1989, pp. 2186-2189 (pp. 18-19).

Jordan, Richard F. et al., "Reactive Cationic Dicyclopentadienylzirconium (IV) Complexes", *Journal of American Chemical Society*, vol. 108, pp. 1718-1719, 1986.

Jordan, Richard F. et al., "Ethylene Polymeriaation by a Cationic Dicyclopentadienylzirconium(IV Alkyl Complex", *Journal of American Chemical Society*, vol. 108, pp. 7410-7411, 1986.

*Primary Examiner*—Schofer: Joseph L.
*Assistant Examiner*—David Wu
*Attorney, Agent, or Firm*—William D. Jackson; Jim D. Wheelington; M. Norwood Cheairs

[57] ABSTRACT

Syndiospecific catalysts and processes for the syndiotactic propagation of a polymer chain derived from an ethylenically unsaturated monomer which contains 3 or more carbon atoms or is a substituted vinyl compound. The catalysts comprise an unbalanced metallocene cation having sterically dissimilar ring structures joined to a positively charged coordinating transition metal atom and a stable noncoordinating counter anion for the metallocene cation. Both ring structures are substituted cyclopentadienyl rings and one is sterically different from the other. Both are in a stereorigid relationship to the coordinating transition metal atom to prevent rotation of the rings by direct stearic hindrence between the ring structures. The catalyst is contacted with a C3+ alpha olefin or other ehtyleically unsaturated compound in a polymerization reaction zone and maintained in contact with the catalyst in the reaction zone under polymerization conditions to produce a syndiotactic polymer.

16 Claims, No Drawings

PROCESS AND CATALYST FOR PRODUCING SYNDIOTACTIC POLYMERS

This application is a division of pending prior application Ser. No. 876,714, filed Apr. 24, 1991 now U.S. Pat. No. 5,223,467 which is a continuation of application Ser. No. 418,497, filed Oct. 10, 1989, abandoned, which, in turn, is a continuation-in-part of application Ser. No. 220,007, filed Jul. 15, 1988, and now U.S. Pat. No. 4,892,851.

TECHNICAL FIELD

This invention relates to catalysts and processes for the production of syndiotactic polymers from ethylenically unsaturated compounds and more particularly to the production of a syndiotactic polyolefin by polymerization of propylene or higher alpha olefin over a stereorigid cationic metallocene catalyst having dissimilar cyclopentadienyl rings.

BACKGROUND OF THE INVENTION

Syndiotacticity is one of a number of stereospecific structural relationships which may be involved in the formation of the stereorigid polymers which may be derived from various monomers. Stereo-specific propagation may be applied in the polymerization of ethylenically unsaturated monomers such as C3+ alpha-olefins, 1-dienes such as 1,3-butadiene and additional or substituted vinyl compounds such as vinyl aromatics, e.g., styrene or vinyl chloride, vinyl ethers such as alkyl vinyl ethers, e.g., isobutyl vinyl ether, or even aryl vinyl ethers. Stereospecific polymer propagation is probably of most significance in the production of polypropylene of isotactic or syndiotactic structure.

Syndiotactic polymers have a unique stereochemical structure in which monomeric units having enantiomorphic configuration of the asymmetrical carbon atoms follow each other alternately and regularly in the main polymer chain. Syndiotactic polypropylene was first disclosed by Natta et al. in U.S. Pat. No. 3,258,455. As disclosed in this patent, syndiotactic polypropylene can be produced by using a catalyst prepared from titanium trichloride and diethyl aluminum monochloride. A later patent to Natta et al., U.S. Pat. No. 3,305,538, discloses the use of vanadium triacetylacetonate or halogenated vanadium compounds in combination with organic aluminum compounds for producing syndiotactic polypropylene. U.S. Pat. No. 3,364,190 to Emrick discloses the use of a catalyst system composed of finely divided titanium or vanadium trichloride, aluminum chloride, a trialkyl aluminum and a phosphorus-containing Lewis base in the production of syndiotactic polypropylene.

As disclosed in these patent references and as known in the art, the structure and properties of syndiotactic polypropylene differ significantly from those of isotactic polypropylene. The isotactic structure is typically described as having the methyl groups attached to the tertiary carbon atoms of successive monomeric units on the same side of a hypothetical plane through the main chain of the polymer, e.g., the methyl groups are all above or below the plane. Using the Fischer projection formula, the stereochemical sequence of isotactic polypropylene is described as follows:

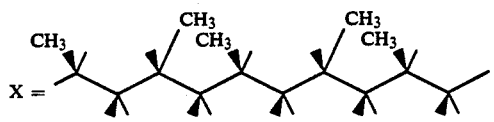

Another way of describing the structure is through the use of NMR. Bovey's NMR nomenclature for an isotactic pentad is ... mmmm ... with each "m" representing a "meso" dyad or successive methyl groups on the same side in the plane. As known in the art, any deviation or inversion in the structure of the chain lowers the degree of isotacticity and crystallinity of the polymer.

In contrast to the isotactic structure, syndiotactic polymers are those in which the methyl groups attached to the tertiary carbon atoms of successive monomeric units in the chain lie on alternate sides of the plane of the polymer. Syndiotactic polypropylene shown in zig-zag representation as follows:

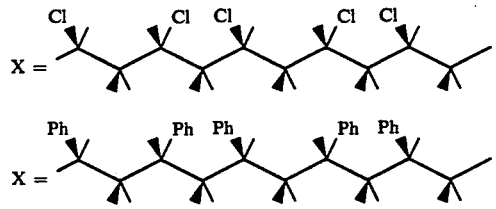

Corresponding representations for syndiotactic polyvinylchloride and polystyrene respectively are:

Using the Fischer projection formula, the structure of a syndiotactic polymer or polymer block for polypropylene is designated as:

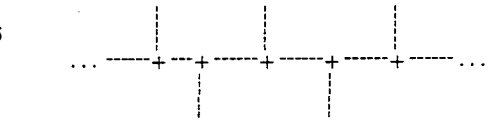

In NMR nomenclature, this pentad is described as ... rrrr ... in which each "r" represents a "racemic" dyad, i.e., successive methyl groups on alternate sides of the plane. The percentage of r dyads in the chain determines the degree of syndiotacticity of the polymer.

Syndiotactic polymers are crystalline and, like the isotactic polymers, are insoluble in xylene. This crystallinity distinguishes both syndiotactic and isotactic polymers from an atactic polymer that is soluble in xylene. An atactic polymer exhibits no regular order of repeating unit configurations in the polymer chain and forms essentially a waxy product.

While it is possible for a catalyst to produce all three types of polymers, it is desirable for a catalyst to produce predominantly isotactic or syndiotactic polymer with very little atactic polymer. Catalysts that produce isotactic polyolefins are disclosed in copending U.S. patent application Ser. Nos. 034,472 filed Apr. 3, 1987; 096,075 filed Sep. 11, 1987 and now U.S. Pat. No.

4,794,096; and 095,755 filed on Sep. 11, 1987 and now U.S. Pat. No.4,975,403. These applications disclose chiral, stereorigid metallocene catalysts that polymerize olefins to form isotactic polymers and are especially useful in the polymerization of a highly isotactic polypropylene.

Catalysts that produce syndiotactic polypropylene or other syndiotactic polyolefins are disclosed in the aforementioned U.S. Pat. No. 4,892,851. These catalysts are bridged stereorigid metallocene catalysts.

The catalysts have a structural bridge extending between dissimilar cyclopentadienyl groups and may be characterized by the formula:

$$R''(CpR_n)(CpR'm)MeQ_k \qquad (1)$$

In formula (1),
Cp represents a cyclopentadienyl or substituted cyclopentadienyl ring; and R and R' represent hydrocarbyl radicals having 1-20 carbon atoms;
R'' is a structural bridge between the rings imparting stereorigidity to the catalyst; Me represents a transition metal and Q a hydrocarbyl radical or halogen;
R'm is selected so that (CpR'm) is a sterically different substituted cyclopentadienyl ring than (CpRn);
n varies from 0 to 4 (0 designating no hydrocarbyl groups, i.e. an unsubstituted cyclopentadienyl ring) and m varies from 1-4, and K is from 0-3. The sterically different cyclopentadienyl rings produces a predominantly syndiotactic polymer rather than an isotactic polymer.

Metallocene catalysts of yet another type are cationic catalysts as disclosed in European Patent Applications 277,003 to Turner et al. and 277,004 to Turner. As disclosed in these applications, a bis(cyclopentadienyl) zirconium, titanium or hafnium compound is reacted with a second compound comprising a cation capable of donating a proton or an ion exchange compound comprising a cation which will irreversible react with a ligand on the first compound, and a bulky, stable anion. The catalysts described in the European Patent Applications 277,003 and 277,004 are disclosed as especially useful in the polymerization of ethylene and more generally in the polymerization of alpha olefins, diolefins and/or an acetylenically unsaturated compounds containing from 2-18 carbon atoms. Principally disclosed in the European applications is the polymerization of ethylene or the copolymerization of ethylene with propylene or 1-butene or with propylene and 1-butene or 1,4 hexadiene. Stereospecificity, or lack thereof, of the polymers as disclosed in the Turner and Turner et al. applications is not generally discussed, although in Application 277,004 examples are given of producing atactic polypropylene and in one instance (Example 39) isotactic polypropylene.

SUMMARY OF THE INVENTION

In accordance with the present invention, there are provided syndiospecific catalysts and processes for the syndiotactic propagation of a polymer chain derived from an ethylenically unsaturated monomer which contains 3 or more carbon atoms or is a substituted vinyl compound. Catalysts in accordance with the present invention comprise an unbalanced metallocene cation and a stable noncoordinating counter anion for the metallocene cation. The metallocene cation is characterized by a cationic metallocene ligand having sterically dissimilar ring structures joined to a positively charged coordinating transition metal atom. Both ring structures are substituted cyclopentadienyl rings and one of the ring structures is a substituted cyclopentadienyl group which is sterically different from the other substituted cyclopentadienyl group. Both of said cyclopentadienyl groups are in a stereorigid relationship relative to the coordinating transition metal atom to prevent rotation of said rings because of direct stearic hindrance between the ring structures.

Syndiotactic polypropylene or other polymers resulting from the polymerization of C3+ alpha olefins or vinyl compounds may be produced in accordance with the method of the present invention. Syndiospecific propagation of the polymer chain is carried out in the presence of a stereorigid cationic metallocene catalyst which incorporates dissimilar substituted cyclopentadienyl rings in direct stearic hindrance with one another so that both are in a stereorigid relationship relative to the coordinating metal atom of the metallocene complex. The catalyst is contacted with a C3+ alpha olefin or other ethylenically unsaturated compound in a polymerization reaction zone and maintained in contact with the catalyst in the reaction zone under polymerization conditions to produce a syndiotactic polymer. The preferred application of the invention is in the production of syndiotactic polypropylene.

Specific catalysts employed in which the aforementioned stereorigid relationship between the dissimilar cyclopentadienyl rings is established in accordance with the present invention may be characterized by the following formula:

$$[(CpS_x)(CpS'y) MeQ_k] + P_a \qquad (2)$$

Wherein:
Cp is a cyclopentadienyl or a substituted cyclopentadienyl ring;
each S is the same or different and is a hydrocarbyl radical having from 1-20 carbon atoms;
each S' is the same or different and is a hydrocarbyl radical having from 1-20 carbon atoms and selected such that CpSx is a sterically different ring than CpSy and is in a sterically hindered relationship relative to catalyst;
Me is a Group 4, 5, or 6 metal from the Periodic Table of Elements;
Q is a hydrocarbyl radical having from 1-20 carbon atoms or is a halogen;
x is from 1 to 5; y is from 1 to 5; k is from 0 to 2; and
$P_a$ is a stable noncoordinating counter ion.

DETAILED DESCRIPTION

The present invention involves certain stereorigid cationic metallocenes and their use as catalysts in syndiotactic polymer propagation. The term metallocene as used herein and in accordance with normal art usage denotes an organometallic coordination compound in which two cyclo-C5 ligands (cyclopentadienyl or substituted cyclopentadienyl rings) are bonded to a central or "sandwiched" metal atom which may be provided by a transition metal or metal halide, alkyl, alkoxy, or alkyl or alkoxy halide or the like. Such structures are sometimes referred to as "molecular sandwiches" since the cyclo-C5 ligands are oriented above or below the plane of the central coordinated metal atom. By the term "cationic metallocene" is meant a metallocene in which the central coordinated metal atom carries a positive charge, that is, the metallocene complex is a cation associated with a stable anion. The cationic metallocenes involved in the present invention are stereorigid. Stereorigidity is imparted to the metallocene complex to prevent rotation of substituted cyclopentadienyl rings about their coordination axes by direct stearic hindrance. That is stereorigidity is imposed by means of substituted cyclopentadienyl rings in which the substituent groups provide for stearic hindrance in the conventional sense of nonbonded spacial interaction between the two substituted cyclopentadienyl rings.

As noted previously, U.S. Pat. No. 4,892,851 discloses the preparation of syndiotactic polypropylene, or other polyolefins, through the use of stereorigid metallocene catalysts. The present invention employs stereorigid metallocene catalysts similar in some respects to those disclosed in U.S. Pat. No. 4,892,851 in the sense that a metallocene ligand is ionized to provide a stable cationic catalyst. The cationic metallocene catalysts employed in the present invention may be prepared following procedures of the type disclosed in the aforementioned European Applications 277,003 and 277,004, but they preferably are prepared by a process employing a triphenylcarbenium borate as discussed in greater detail below. Where procedures of the type disclosed in the European applications are used in the preparation of cationic metallocene catalysts to be employed in the present invention, certain important distinctions must be observed as evidenced by the fact that neither of the European applications disclose the preparation of syndiotactic polymers. Thus, in the metallocene catalysts disclosed in the European applications, the cyclopentadienyl groups may be the same or different, and while they can be bridged, they need not be and, in fact, are usually unbridged. Moreover, to the extent that the metallocene catalysts disclosed in the European applications are bridged to impart stereorigidity, they are also symmetrical. In contrast to the teachings of the Turner European applications, the cationic metallocene catalysts employed in the present invention must not only be stereorigid with stereorigid provided by stearic hindrance, the cyclopentadienyl groups must be dissimilar.

Stereorigid cationic metallocene catalysts employed in the present invention may be characterized by the following formula:

[(CpSx)(CpS'y) MeQk]+Pa    (2)

wherein: Cp, R, R', R'', S, S', T, T', Me, Q, Pa, k, m, n, x and y are as described previously.

In the catalysts of formula (2), stereorigidity is imparted by means of direct stearic hindrance between the two substituted cyclopentadienyl groups provided by relatively bulky or long chain substituents groups represented by S and S'.

The counter anion indicated by P in formula (2) is a compatible noncoordinating anion which may be of the type described in the aforementioned Turner European applications. The anion P either does not coordinate with the metallocene cation or is only weakly coordinated to the cation thereby remaining sufficiently labile to be displaced by a neutral Lewis base. As described in the Turner applications, the term "compatible noncoordinating anion" identifies an anion which when functioning as a stabilizing anion in the metallocene catalyst system does not transfer an anionic substituent or fragment thereof to the cation to form a neutral metallocene and boron byproduct or other neutral metal or metalloid byproduct, as the case may be. Suitable noncoordinating anions include: [W(PhF5)]—, [Mo(PhF5)—] (wherein PhF5 is pentafluoryl phenol) [ClO4]—, [PF6]—, [SbR6]—, [AlR4]— (wherein each R is independently, Cl, a C1-C5-alkyl group, preferably a methyl group, an aryl group, e.g., a phenyl or substituted phenyl group, or a fluorinated aryl group. For a further description of compatible noncoordinating anions and their associated cations which may be employed in the present invention, reference is made to European applications 277,003 and 277,004, the entire disclosures of which are incorporated herein by reference. In considering these disclosures, it must be recalled, however, that unlike the cationic metallocene catalyst of the Turner European applications, the cationic metallocene catalysts employed in the present invention must be stereorigid with dissimilar Cp rings. The size of the counter ion will depend on the bulk of the substituent groups on the cyclopentadienyl rings and the manner in which stereorigidity is imparted to the metallocene structure. Where bridged metallocene structures of the type disclosed in U.S. Pat. No. 4,892,851 are involved, a basic requirement for production of the syndiotactic polymers is that the cyclopentadienyl rings be dissimilar and, of course, at least one ring being substituted. With stereorigidity provided by the bridge structure, monomer insertion and isomerization is controlled primarily by the relationship of the anionic counterion to the bridged structure.

Where as in this invention stereorigidity is imparted by means of direct stearic hindrance between by the cyclopentadienyl substituent groups relatively larger substituent groups are required and stearic relationships are developed not only between the cyclopentadienyl substituents but also between the substituents and the noncoordinating anion. Here, the size of the anionic counterion may be slightly smaller than in the case of a bridged structure where stearic hindrance is not significant, or at least is not as significant, as in nonbridged structure. In addition to size, the other important characteristics of the anionic counterions are stability and bonding. The anion must be sufficiently stable so that it cannot be rendered neutral by virtue of the metallocene cation extracting an anionic substituent or fragment. The bond strength with the cation is such that it must be noncoordinating or only weakly coordinating with the metallocene cation so that it makes way for the inserting monomer in the chain growing reaction.

Preferably, the syndiospecific metallocene catalysts of the present invention exhibit bilateral symmetry of the metallocene ligands when viewed as planar projections of the cyclopentadienyl groups. By the term "bilateral symmetry" as used here, is meant the symmetry of the ligand as viewed through the axes of the substituted or unsubstituted Cp groups. For example, the isopropylidene (fluorenyl) (cyclopenta-dienyl) ligand would exhibit such bilateral symmetry whereas the corresponding structure but with the cyclopentadienyl group substituted at the three position would not exhibit bilateral symmetry. The corresponding ligand with two identical substituents at the 3 and 4 position on the cyclopentadienyl group would have bilateral symmetry.

The metallocene catalysts disclosed in the Turner European applications suffer from certain disadvantages in that Lewis bases may be produced by protonation of the metallocene ligand which function as poisons for the metallocene catalyst. A preferred procedure for producing cationic metallocene catalyst of the type employed in the present invention involves the reaction of an anionic compound in a noncoordinating solvent with a dimethyl metallocene which is unbalanced and stereorigid by virtue of a bridge between the cyclopentadienyl groups or by a sterically hindered relationship between the cyclopentadienyl rings. By way of example, triphenylcarbenium tetrakis (pentafluorophenyl) boronate may be reacted with the neutral metallocene in a solvent such as toluene. Such catalysts and their preparation are disclosed in U.S. patent application Ser. No. 419,046 by John A. Ewen and Michael J. Elder for "Preparation of Metallocene Catalysts for Polymerization of Olefins" filed on even date herewith, the entire disclosure of which in incorporated by reference.

A preferred application of the invention is in the syndiotactic polymerization of C3+ alpha olefins, specifically propylene, but the invention may be employed in the preparation of other polymers from ethylenically unsaturated monomers where syndiotacticity is a desired structure. By the term ethylenically unsaturated monomer as used herein is meant a hydrocarbon or substituted hydrocarbon compound characterized by a terminal vinyl group (CH2=CH—). Such compounds as may be employed in the present invention have at least three carbon atoms or are a substituted vinyl compound, specifically vinyl chloride. They may be characterized in terms of the following formula:

  (5)

wherein: R is a hydrocarbyl group or nonhydrocarbyl substituent. For example, syndiospecific propagation of a polymer chain from 1-butene may be carried out in accordance with the invention. Specific polymers in which syndiotacticity is sometimes desirable and to which the invention is applicable include polyvinyl chloride and polystyrene. The polymerization of a 1-diene such as 1,3-butadiene may also be carried out in accordance with the present invention to achieve a syndiotactic polymer configuration. Syndiotactic polypropylene is probably of the greatest practical significance and the invention will be described in detail with reference to the production of syndiotactic polypropylene. However, other compounds in which the syndiotactic configuration is desirable are also of interest.

Polymerization procedures as disclosed in the aforementioned U.S. Pat. No. 4,892,851 may be employed in carrying out the present invention. Co-catalysts, usually organoaluminum compounds such as trialkylaluminum, trialkyloxyaluminum, dialkylaluminum halides or alkylaluminum dihalides may be employed in the present invention. Especially suitable alkylaluminums are trimethylaluminum and triethylaluminum with the latter, commonly referred to as TEAL, being most preferred. However, aluminoxane which may be used as a cocatalyst in the U.S. Pat. No. 4,892,851 need not be, and preferably is not, used in carrying out the present invention. While applicants' invention is not to be restricted by theory, it is believed that neutral metallocenes of the type disclosed in the parent application form cationic complexes by reaction with the aluminoxane in the manner as disclosed by Zambelli, A. et al., "Isotactic Polymerization of Propene: Homogenous Catalysts Based on Group 4 Metallocenes Without Methylaluminoxane", Macro-Molecules 1989, 22, pages 2186–2189. It is believed that the anionic species derived from the aluminoxane compound may function to stabilize the cationic metallocene to permit monomer insertion chain migration and isomerization during the growth of the polymer chain resulting in syndiotacity. The stereorigid cationic metallocene catalysts employed in the present invention accomplish isomerization during monomer insertion and chain migration.

The procedures and reaction conditions disclosed in the aforementioned U.S. Pat. No. 4,892,851 may be employed in the present invention with the exception, as noted above, that aluminoxanes need not be used and preferably are not used. The prior art discloses the use of aluminoxanes as co-catalysts with metallocene catalysts in amounts well in excess of a stoichiometric equivalent amount providing mole ratios of aluminum to the coordinating metal (Me) of about 100–1000. Aluminoxanes usually are not employed in the present invention and if they are used they are in amounts well below the aforementioned range and preferably providing an Al/Me mole rate of no more than 10 and, more preferably, no more than 1.

The catalysts used in the present invention are syndiospecific and produce a polymer with a high syndiotactic index. As disclosed in U.S. Pat. No. 4,892,851, syndiotactic polymers generally have lower heats of crystallization than the corresponding isotactic polymers. In addition, for the same number of imperfections in the polymer chain, syndiotactic polymers have a higher melting point than isotactic polymers.

The metallocene catalysts used in the present invention may be characterized by formula (2) as described above. Me is a Group 4, 5, or 6 metal from the Periodic Table of Elements but preferably is a Group 4 or 5 metal and more preferably a Group 4 metal, specifically titanium, zirconium or hafnium. Vanadium is the most suitable of the Group 5 metals. Each Q is a hydrocarbyl radical having 1–20 carbon atoms or is a halogen. As a practical matter, Q will usually be a methyl or ethyl group or a halide, preferably chlorine. In order to be syndiospecific, the Cp rings in the metallocene catalysts must be substituted in a substantially different manner so that there is a stearic difference between the two Cp rings, and therefore, S'y is selected such that (CpS'y) is a substantially different substituted ring than (CpSx). In order to produce a syndiotactic polymer, the characteristics of the groups substituted directly on the cyclopentadienyl rings appear important. Thus, by "stearic difference" or "sterically different" as used herein, it is intended to denote a difference between the stearic characteristics of the Cp rings that controls the approach of each successive monomer unit that is added to the polymer chain. The stearic difference between the Cp rings acts to block the approaching monomer from a random approach and controls the approach such that the monomer is added to the polymer chain in the syndiotactic configuration.

Without intending to limit the scope of the present invention as indicated by the claims, it is believed that in the polymerization reaction, both the catalyst and the approaching monomer units isomerize with each monomer addition to the polymer chain as the chain migrates between catalyst sites. This isomerization of the monomer which is controlled by the stearic blockage of the differently substituted Cp rings results in the alternating configuration characteristic of syndiotactic polymers and is in contrast to the chain-end control of the catalysts disclosed by Natta et al. The different reaction mechanism also results in a different structure for the polymer.

In the preferred catalysts for use in the present invention, Me is titanium, zirconium or hafnium; Q is a hydrocarbyl group, preferably methyl, or halogen, preferably chlorine; and k is preferably 1, but it may vary with the valence of the metal atom. Exemplary hydrocarbyl radicals in addition to methyl include ethyl, propyl, isopropyl, butyl, isobutyl, amyl, isoamyl, hexyl, heptyl, octyl, nonyl, decyl, cetyl, phenyl, and the like. Other hydrocarbyl radicals useful in the present catalysts include other alkyl, aryl, alkenyl, alkylaryl or arylalkyl radicals. Further Sx and S'y, may comprise hydrocarbyl radicals attached to a single carbon atom in the Cp ring as well as radicals that are bonded to two carbon atoms in the ring. The catalysts used in the present invention may be derived from a neutral metallocene moiety prepared in accordance with procedures such as disclosed in U.S. Pat. No. 4,892,851 which is then converted to the cationic state, following procedures such as disclosed in the aforementioned European applications 277,003 and 277,004 or more preferably by reaction with triphenylcarbenium boronates as described in the aforementioned copending application Ser. No. 419,046.

As noted previously for metallocene catalysts of formula (2) stereorigidity is imparted by stearic hindrance due to nonbonded interaction between the two substituted cyclopentadienyl rings. Stereorigidity is provided due to the fact that the substituent groups of the cyclopentadienyl rings interact in a special arrangement between rings such that rotation of the rings relative to the zirconium or other transition metal atom is prevented or at least retarded to a substantial extent. Nonbridged neutral metallocene precursors for the catalysts of formula (2) may be prepared from substituted cyclopentadienyl radicals in accordance with procedures described hereinafter. Examples of such neutral metallocenes providing for direct stearic hindrance include metallocenes of transition metals as described previously, preferably hafnium, zirconium or titanium, in which the metallocene ligand includes ring structures having two or more substituents with a total of at least five substituents on both cyclopentadienyl rings. Examples include (dialkyl cyclopentadienyl), (trialkylcyclopentadienyl) (trialkylcyclopentadienyl) (tetraalkylcyclopentadienyl) groups. Other substituted cyclopentadienyl radical pairs forming the ligand include di substituted, tetra substituted ring pairs, tri substituted, tetra substituted ring pairs, and di substituted penta substituted ring pairs. Suitable ligand structures include (1,2 dialkylcyclopentadienyl) (1,3,4, trialkylcyclopentadienyl), (1,2 dialkylcyclopentadienyl) (1,3,4, trialkylcyclopentadienyl), (1,3 dialkylcyclopentadienyl) (1,3,4 trialkylcyclopentadienyl), (1,2 dialkylcyclopentadienyl) (1,3,4 trialkylcyclopentadienyl), (1,2,3 trialkylcyclopentadienyl), (tetraalkylcyclopentadienyl), (1,2 dialkylcyclopentadienyl) (tetralkylcyclopentadienyl), (1,2,4 trialkylcyclopentadienyl), (tetralkylcyclopentadienyl), (1,3 dialkyl cyclopentadienyl) (1,2,3,4 tetralkyl cyclopentadienyl), (1,3 dialkyl cyclopentadienyl) (pentalkyl cyclopentadienyl). The corresponding alkylsilyl substituted cyclopentadienyl groups may also be used in forming the metallocene ligand. Specific substituent groups which may be employed in providing direct stearic hindrance of the metallocene catalyst include: CH3—, C2H5—, C3H7—, (CH3)3C—, (CH3)3CH2—, (CH3)3Si—, (C2H5)3C—(C2H5)3C CH2—, (C2H5)3Si—. Specific examples of sterically hindered ligand structures include (1,3 dipropylcyclopentadienyl) (1,2,4 triethylcyclopentadienyl) and (1,2 diisobutylcyclopentadienyl) (triethylcyclopentadienyl). As indicated previously, the preferred transition metals in formulating the metallocene catalysts are zirconium, hafnium and titanium. Also, condensed ring cyclopentadienyl structures can be used in providing the metallocene ligands as depicted by formula (3). Specifically, the Cp ring structures may include substituted fluorenyl and indenyl groups.

In the sterically hindered metallocene catalysts of the present invention, any suitable technique can be used to produce the substituted cyclopentadienyl groups which may be lithiated, for example, following a protocol such as disclosed in U.S. Pat. No. 4,892,851, for reaction with a transition metal chloride to form the neutral ligand which is then converted to the cationic state. However, in formulating the neutral metallocene precursors for later conversion to the cationic metallocenes of formula (2), the lithiated substituted cyclopentadienyl groups are reacted stepwise with the transition metal salt, e.g., zirconium or titanium tetrachloride, with the product of this reaction reacted with the other dissimilar substituted cyclopentadienyl group. By way of example using the conventions Cp' and C" to designated dissimilar cyclopentadienyl groups having bulky and/or sterically hindered substituents as described above, a lithiated Cp' group may be reacted with zirconium tetrachloride to produce the dicyclopentadienyl (Cp'2) ZrCl2. The resulting product may be chlorinated to produce the monocyclopentadienyl zirconium trichloride and this product (Cp'ZrCl3) then reacted with the lithiated Cp" group to produce the product (Cp'), (Cp") ZrCl2. Those skilled in the art will recognize that this stepwise reaction formate can be followed to produce metallocene based upon titanium, hafnium, vanadium or other suitable transition metals.

Substituted cyclopentadienyl groups from which the metallocene ligands of formula (2) are formed can be derived by any suitable technique. Suitable starting materials include benzyl alcohol, ketones of substituted cyclopentadienes and substituted fulvenes. By way of example, a penta substituted cyclopentadiene can be produced by reaction of 5 moles of the appropriate alcohol with 1 mole of cyclopentadiene in the presence of particulate sodium. The sodium acts to promote ring aromitization as is well known in the art.

The reaction of methyl lithium or another alkyl lithium with a tetra substituted dimethylfulvene may be employed to arrive at substituted cyclopenta-dienyl group. For example, tetraalkyl-6-dimethyl-fulvene may be reacted with methyl lithium or ethyl lithium to produce tertbutyl tetraalkyl cyclopentadiene or tertamyl tetraalkyl cyclopentadiene, respectively. The resulting substituted cyclopentadienes can be reacted through the previously described stepwise procedure with a transition metal halide, e.g., titanium hafnium or zirconium tetrachloride, to produce the corresponding dichloride in which dissimilar substituted cyclopentadienyl groups are coordinated with the titanium, zirconium or other transition metal in the neutral metallocene complex. It will recognized from the foregoing that numerous metallocene ligands having bulky substituted cyclopentadienyl groups can be prepared following the reaction formats indicated above.

Another synthesis procedure involves the formation of substituted cyclopentenones by cyclization or ring closure reactions involving or esters. The cyclization reaction can be carried out in accordance with any suitable procedure to produce the corresponding cyclopentanone. The substituted cyclopentenone may be reduced to an alcohol by any of the well known reduction reactions for conversion of cyclic ketones to the corresponding alcohols. For example, lithium or sodium aluminum hydride can be employed to reduce the substituted cyclopentenone to the corresponding substituted cyclopentenol. A dehydrating agent such as sulfuric acid or oxalic acid can then be used to dehydrate the substituted cyclopentenol to the corresponding substituted cyclopentadiene. The reaction of polyphosphoric acid on substituted alpha-ethylenic esters can be used for the preparation of substituted cyclopentedienes used in formulating sterically hindered metallocenes of Formula (2). Examples include reactions of polyphosphoric acid on substituted acrylates or crotonates. For example, methyl-2-n-butyl crotonate, isopropyl crotonate, or butyl crotonate can be reacted with polyphosphoric acid to produce the corresponding substituted cyclopentenones. These reactions can take place at temperatures in the range of 60°-100° C. with the reaction times varying from a few minutes to a few hours. The resulting ketones are reduced by LiAlH4 to the corresponding alcohols and the alcohols then dehydrated to yield the desired substituted cyclopentadienes. These, in turn, can be aromatized and reacted with the appropriate transition metal halide, for example titanium, hofnium or zirconium tetrachloride to produce the metallocenes. Similar reactions with polyphosphoric acid can be carried using acrylic esters, e.g., methylacrylate.

The neutral metallocenes can be converted to the cationic state by any suitable technique. Preferably, such conversion is affected using a trityl compound such as triphenylcarbenium tetrakis (pentafluorolphenyl borate) as described above. Other suitable techniques are disclosed in the aforementioned European applications 277,003 and 277,004.

Having described specific embodiments of the present invention, it will be understood that modification thereof may be suggested to those skilled in the art, and it is intended to cover all such modifications as fall within the scope of the appended claims.

I claim:

1. A process for the syndiotactic propagation of a polymer chain derived from an ethylenically unsaturated monomer comprising:
   (a) providing a catalyst comprising an unbalanced metallocene cation and a stable noncoordinating counter anion for said metallocene cation, said metallocene cation being characterized by a cationic metallocene ligand having sterically dissimilar ring structures joined to a positively charged coordinating transition metal atom; and each of said ring structures being a substituted cyclopentadienyl group and one of said ring structures being a substituted cyclopentadienyl group which is sterically different from the other cyclopentadienyl group, and both of said substituted cyclopentadienyl groups being in a sterically hindered relationship which each other providing a stereorigid relationship relative to said coordinating transition metal atom to prevent rotation of said rings.
   (b) contacting said catalyst in a polymerization reaction zone with an ethylenically unsaturated monomer which contains 3 or more carbon atoms or which is a substituted vinyl compound and maintaining said reaction zone under polymerization conditions to produce syndiospecific polymerization of said monomer.

2. The process of claim 1, wherein the transition metal of said catalyst is titanium, zirconium or hafnium.

3. The method of claim 1, wherein said ethylenically unsaturated monomer is a vinyl aromatic compound.

4. The method of claim 3, wherein said vinyl aromatic compound is styrene.

5. The method of claim 1, wherein said ethylenically unsaturated monomer is a substituted vinyl compound.

6. The method of claim 5, wherein said substituted vinyl compound is vinyl chloride.

7. The method of claim 1, wherein said ethylenically unsaturated monomer is a C3-C4 alpha olefin.

8. The method of claim 7, wherein said C3-C4 alpha olefin is propylene.

9. A process for the production of syndiotactic polypropylene comprising;
   (a) providing a stereorigid cationic metallocene catalyst characterized by the formula:

$[(CpSx)(CpS'y)MeQk]^+ Pa^-$ wherein:
   Cp is a substituted cyclopentadienyl ring;
   each S is the same or different and is a hydrocarbyl radical having from 1-20 carbon atoms;
   each S' is the same or different and is a hydrocarbyl radical having from 1-20 carbon atoms and selected such that CpSx is a sterically different ring than CpS'y and is in a sterically hindered relationship relative to CpS'y sufficient to prevent rotation of said rings and impart stereorigidity to said catalyst;
   each Q is a hydrocarbyl group having 1-20 carbon atoms or is a halogen;
   Me is a Group 4, 5, or 6 metal from the Periodic Table of Elements;
   x is 1 to 5; y is from 1 to 5; k is from 0 to 2; and Pa$^-$ is a stable noncoordinating counter anion
   (b) contacting said catalyst with propylene in a polymerization reaction zone and maintaining said reaction zone under polymerization reaction conditions to produce syndiotactic polypropylene.

10. The process of claim 9, wherein Me is a titanium, zirconium, or hafnium and K is 1.

11. The process of claim 10, wherein Q is a methyl or ethyl group or is a halogen.

12. The method of claim 11, wherein Q is a methyl group or chlorine.

13. The method of claim 11, wherein x is 2 or 3, and y is 3-5.

14. The method of claim 13, wherein S and S' are alkyl or alkysilnayl groups, containing from 1-8 carbon atoms.

15. The process of claim 9, wherein the polymerization of Step b is carried out under conditions in which any aluminoxane concentration is maintained at a level providing Al/Me mole ratio of no more than 10.

16. The method of claim 15, wherein the polymerization in Step b is carried out in the absence of added aluminoxane.

* * * * *